(12) United States Patent
Cardoso De Lima et al.

(10) Patent No.: US 11,529,298 B2
(45) Date of Patent: Dec. 20, 2022

(54) COSMETIC COMPOSITION AND ITS USE, DERMOCOSMETIC FORMULATION

(71) Applicant: LUXBIOTECH FARMACÊUTICA LTDA, Jaguariuna (BR)

(72) Inventors: Erine Cardoso De Lima, Hortolândia (BR); Talitha Farina Bezerra, Hortolândia (BR); Luiz Felipe De Oliveira Stehling, Hortolândia (BR); Silvana Masiero, Hortolândia (BR)

(73) Assignee: LUXBIOTECH FARMACÊUTICA LTDA, Jaguariuna (BR)

( * ) Notice: Subject to any disclaimer, the term of this patent is extended or adjusted under 35 U.S.C. 154(b) by 182 days.

(21) Appl. No.: 17/005,452

(22) Filed: Aug. 28, 2020

(65) Prior Publication Data

US 2021/0059917 A1  Mar. 4, 2021

(30) Foreign Application Priority Data

Aug. 28, 2019  (BR) .................. 10 2019 017936 8

(51) Int. Cl.
*A61K 8/44* (2006.01)
*A61K 8/97* (2017.01)
*A61K 8/37* (2006.01)
*A61K 8/34* (2006.01)
*A61K 8/19* (2006.01)
(Continued)

(52) U.S. Cl.
CPC .................. *A61K 8/44* (2013.01); *A61K 8/19* (2013.01); *A61K 8/34* (2013.01); *A61K 8/362* (2013.01); *A61K 8/365* (2013.01); *A61K 8/37* (2013.01); *A61K 8/86* (2013.01); *A61K 8/922* (2013.01); *A61K 8/97* (2013.01); *A61Q 17/04* (2013.01); *A61Q 19/08* (2013.01); *A61K 2800/522* (2013.01); *A61K 2800/524* (2013.01); *A61K 2800/59* (2013.01)

(58) Field of Classification Search
CPC . A61K 8/19; A61K 8/34; A61K 8/345; A61K 8/362; A61K 8/365; A61K 8/37; A61K 8/375; A61K 8/44; A61K 8/442; A61K 8/49; A61K 8/4913; A61K 8/4946; A61K 8/60; A61K 8/73; A61K 8/86; A61K 8/922; A61K 8/97; A61K 8/9761; A61K 8/9789; A61K 8/9794; A61K 2800/522; A61K 2800/524; A61K 2800/59; A61Q 17/04; A61Q 19/08
See application file for complete search history.

(56) References Cited

U.S. PATENT DOCUMENTS

2009/0068255 A1\*  3/2009  Yu ........................... A61P 35/00
424/59

OTHER PUBLICATIONS

Wan, H. et al. "A study of the reproducibility of the MTT test", Journal of materials science 1994; 5:154-159.
(Continued)

*Primary Examiner* — Isaac Shomer
*Assistant Examiner* — Amanda Michelle Petritsch
(74) *Attorney, Agent, or Firm* — Meunier Carlin & Curfman LLC (57) ABSTRACT

The present invention relates to dermocosmetic formulations for use in combating skin aging, especially photoaging. The present invention promotes the increase of the synthesis of collagen, elastin and glycosaminoglycans (GAG), in addition to significantly increase the activity of the superoxide dismutase enzyme (SOD) and the cell proliferation.

24 Claims, 3 Drawing Sheets

(51) Int. Cl.
*A61K 8/362* (2006.01)
*A61K 8/92* (2006.01)
*A61K 8/86* (2006.01)
*A61Q 17/04* (2006.01)
*A61Q 19/08* (2006.01)
*A61K 8/365* (2006.01)

(56) References Cited

OTHER PUBLICATIONS

Bank, U. et al. "Measurement of cellular activity with the MTT test", Optimization of the method., Allerg immunol; 1991 37(3-4): 119-23 [English abstract only].

* cited by examiner

COSMETIC COMPOSITION AND ITS USE, DERMOCOSMETIC FORMULATION

FIELD OF THE INVENTION

The present invention is directed to the development of a dermocosmetic formulation for use in combating skin aging, especially photoaging. The present invention acts to increase the synthesis of collagen, elastin and glycosaminoglycans (GAG), in addition to significantly increase the activity of the superoxide dismutase enzyme (SOD) and cell proliferation.

BACKGROUND OF THE INVENTION

Skin aging can be classified in two ways:
Intrinsic aging—or, as it is also known, chronological aging, is dependent on the genetics of each individual and, according to the name, is caused by time.
Extrinsic aging—it is the one that results from factors external to the individual, that is, it can be caused by exposure of the skin to agents such as pollution, inadequate nutrition, but mainly, sun exposure.

When aging is caused by sun exposure, it is called photoaging. This type of aging causes the appearance of spots on the skin, among other effects on the appearance of the skin.

The search for substances that can slow or reverse the skin aging process is a constant tool for research and development in the dermocosmetic area. In view of these circumstances, the evaluation of the efficacy of compounds with antioxidant, immunomodulatory, protective and regulating activities of cutaneous homeostasis has contributed to attenuate the aesthetic manifestations resulting from the accelerated aging process, especially photoaging.

The serious appearance of the aging process is due, among other things, to the drastic histological changes represented mainly by deep atrophy of the dermal architecture and destruction of important protein structures of the extracellular matrix (MEC)—especially collagen, elastin and glycosaminoglycans (GAG)—, resulting in changes that are often malignant or irreversible.

Collagen and elastin form a three-dimensional network that constitutes the base architecture of the dermis, in which other substances and different cell types are dispersed. Collagen is the most abundant macromolecule of the connective tissue and its main functions are to guarantee the mechanical property and structural integrity of tissues. Elastin is characterized by providing physical resistance to the skin and its structure is especially involved in flexibility and plasticity. The polyanionic structure of GAG provides hydration retention power and is also responsible for interactions between MEC and dermis cells, influencing the signaling, differentiation and cell proliferation processes. GAG molecules surround collagen, elastin and dermis cells, especially fibroblasts, attaching themselves to water molecules, conferring hydration to skin proteins.

Still, free radicals such as superoxides and hydroxyl radicals are formed by the oxidative phosphorylation process and cause damage to lipid, protein and mainly nucleic acid cell constituents. In order to try to reverse the harmful oxidative process, a mechanism called redox homeostasis, is used by cells as an endogenous defense, and consists of the balance between the production of free radicals and their elimination by various antioxidant compounds and enzymes. This mechanism includes the enzymes superoxide dismutase (SOD), glutathione peroxidase and catalase, in addition to non-enzymatic reducing agents.

In order to solve the problem of combating photoaging, several non-therapeutic techniques and forms of treatment are suggested in the literature and by another important segment, the cosmetic industry, which promotes treatments that use active ingredients incorporated in creams, cosmetic compositions, gels, elixirs among others.

For example, the document BR 11 2012 007598 5 discloses a topical composition intended for the treatment of photoaging. However, in said document, there are no teachings or data that suggest the dermocosmetic composition of the present invention and that acts in increasing the synthesis of collagen, elastin and glycosaminoglycans (GAG), besides significantly increasing the activity of the superoxide dismutase enzyme (SOD) and, mainly, cell proliferation.

Thus, there is an urgent need for the development of a dermocosmetic formulation that acts as an antioxidant, and that is immunomodulatory, protective and regulates the cutaneous homeostasis, in order to be verified as an effect of combating photoaging, the increase of collagen, elastin and glycosaminoglycans (GAG) synthesis, in addition to the significant increase in the activity of the superoxide dismutase enzyme (SOD) and cell proliferation, measurable via quantification of the compound bromodeoxyuridine (BrdU). The quantification via BrdU is done in tests on human fibroblasts, which are responsible for the production of collagen, elastin and epithelial growth factors, significantly minimizing the photoaging effect and is superior to what is currently known in the state of the art.

SUMMARY OF THE INVENTION

The present invention relates to dermocosmetic formulations for use in combating skin aging, especially photoaging. The present invention promotes the increase of the synthesis of collagen, elastin and glycosaminoglycans (GAG), in addition to significantly increase the activity of the superoxide dismutase enzyme (SOD) and cell proliferation.

A preferred embodiment of the invention relates to dermocosmetic formulations that act as antioxidants, immunomodulators, protectors and regulators of cutaneous homeostasis.

Another embodiment of the invention relates to the cosmetic composition containing a combination of actives such as amino acids, botanical extracts, esters and glycols, which act to combat skin aging, especially photoaging.

In another preferred embodiment of the invention, the use of said cosmetic composition to combat skin aging, in particular photoaging, is described.

Surprisingly, the inventors of the present invention have identified an excellent performance of the formulations described herein in the protein synthesis, in particular, in the synthesis of proteins collagen, elastin and GAGs, which help to decrease and attenuate the aspects and signs of skin aging, especially photoaging. Furthermore, said formulations increase the activity of the superoxide dismutase enzyme (SOD), which means that said formulations have a high antioxidant property. In addition, these formulations also have the effect of increasing cell proliferation. All of these effects have the consequence of acting not only in stimulating the production of collagen and elastin, but also acting as an antioxidant fighting free radicals and as a moisturizer, improving the skin condition in a superior and surprising way.

These features of the invention will be described in more detail in the detailed description of the invention.

DETAILED DESCRIPTION OF THE INVENTION

In this description, a dermocosmetic formulation, a cosmetic composition and its use to combat skin aging, in particular photoaging, are presented. Said cosmetic composition comprises the combination of several actives, such as skin conditioning agents, such as amino acids, botanical extracts, esters and glycols, in addition to other components.

Collagen, elastin and GAGs are part of the proteins that allow structuring the firmness, resistance and hydration of the skin. In the aging process and exposure to ultraviolet (UV) radiation, this structural content is lost or reduced, which causes the appearance of the classic signs of aging: flaccidity, wrinkles, fragile, thin and dehydrated skin.

Cell proliferation is verified through studies with fibroblasts. Fibroblasts are cells of mesenchymal origin whose function is the synthesis of fibrillar (collagen and elastin) and non-fibrillar (glycoproteins and proteoglycans) components of the extracellular matrix of connective tissue. These cells also have the function of producing growth factors and have the potential to differentiate into highly specialized cells. Therefore, its importance in the matter of skin aging is so great.

UV rays damage collagen fibers and, consequently, cause sagging skin among other problems.

A dermocosmetic formulation that protects the existing collagen from the negative action of UV radiation and which also increases the proliferation of cells responsible for the production of the collagen and elastin itself, is a formulation that will act strongly in the fight against skin aging, especially photoaging, because by enabling the increase of these mentioned structures, it recovers the levels of these fibrillar and non-fibrillar components, in addition to reducing the signs and symptoms of aging.

Surprisingly, the inventors of the present invention noticed that the said cosmetic composition acts in order to increase the protein synthesis, in particular, of collagen, elastin and GAGs, besides increasing the activity of the superoxide dismutase enzyme (SOD) and also acting in the increase of the cell proliferation. Therefore, in addition to acting on the fibers already formed, improving their general condition, the said composition stimulates the proliferation of cells that precisely produce collagen and elastin, making the effect of the composition doubly effective.

The dermocosmetic formulation of the composition is carried out by combining several skin conditioning agents, such as amino acids, botanical extracts, esters and glycols.

Examples of conditioning agents can be: PCA Sodium, Sodium Lactate, Arginine, Aspartic Acid, PCA, Glycine, Alanine, Serine, Valine, Proline, Threonine, Isoleucine, Histidine, Phenylalanine, *Olea europaea* Leaf Extract (olive tree), Butylene Glycol, *Prunus mume* Fruit Extract, Silanetriol, Ramnose, *Medicago sativa* extract (Alfalfa), Ethylhexylglycerin, Glycerin, *Microcitrus australasica* extract, Gum-1 biosaccharide, Gum-2 biosaccharide, *Physalis angulata* extract, Caprylic, Capric Triglyceride; Fruit Extract of Citrus aurantium bergamia; *Cupressus sempervirens* leaf/stem extract; *Plumeria rubra* Flower Extract; Rose extract; *Rosmarinus officinalis* Leaf Extract; *Vanilla Planifolia* Fruit Extract, Glycine Soybean Seed Extract, Cetearyl Olivate.

Preferably, the formulation of the cosmetic composition is carried out by combining Sodium PCA, Sodium Lactate, Arginine, Aspartic Acid, PCA, Glycine, Alanine, Serine, Valine, Proline, Threonine, Isoleucine, Histidine, Phenylalanine, *Olea europaea* leaf extract (olive tree), Butylene Glycol, *Prunus* Mume fruit extract, Silanetriol, Ramnose, *Medicago sativa* extract (Alfalfa), Ethylhexylglycerin, Glycerin, *Microcitrus australasica* fruit extract, Gum-1 Biosaccharide, Gum-2 Biosaccharide, *Physalis angulata* Extract, Caprylic, Capric Triglyceride.

The dermocosmetic formulation of the present invention acts to increase the production of collagen and elastin in two ways: (i) protecting the fibers from the damage of UV radiation, even without being a sunscreen and; (ii) increasing the proliferation of cells that produce these proteins, which are fibroblasts.

SOD is a fundamental enzyme in the defense of the organism against reactive oxygen species, called free radicals, and acts in the removal of the superoxide radical.

Different types of stressor agents such as pollution, intrinsic aging and UV radiation itself promote in cells an "oxidative explosion", which constitutes the production of reactive oxygen species (ROS), mainly in the production of superoxide anion ($O_2 \bullet -$) and hydrogen peroxide ($H_2O_2$). These EROs activate molecules for the induction of defense genes and the polymerization of proteins that make up the cell wall, in addition to stimulating the production of physiological antioxidative enzymes such as SOD, which neutralizes EROS by promoting oxide-reduction reactions and avoiding that inflammation mediators are released. In addition, it prevents lipid peroxidation by protecting epithelial cells from aging.

The dermocosmetic formulation of the present invention containing Sodium PCA, Sodium Lactate, Arginine, Aspartic Acid, PCA, Glycine, Alanine, Serine, Valine, Proline, Threonine, Isoleucine, Histidine, Phenylalanine, *Olea europaea* leaf extract (olive tree), Butylenglycol, *Prunus* mume Fruit Extract, Silanetriol, Ramnose, *Medicago sativa* extract (Alfalfa), Ethylhexylglycerine, Glycerin, *Microcitrus australasica* Fruit Extract, Gum-1 biosaccharide, Gum-2 biosaccharide, *Physalis angulata* extract, Caprylic, Capric triglyceride, demonstrated strong action on protein synthesis, especially collagen, elastin and GAGs, in addition to increasing the activity of the SOD enzyme and increasing cell proliferation, which represents a surprising and unexpected result.

In accordance with the present invention, the terms "active substance", "active ingredient" and "active" are used interchangeably and refer to the compounds in a cosmetic composition that promote a desired cosmetic effect.

According to the present invention, the term "cosmetically acceptable" refers to compounds that are commonly used in the cosmetic technique in conjunction with active ingredients. Particularly, "cosmetically acceptable" refers to compounds which give, without limitation, shape, aroma, stability and coloring to the final cosmetic composition, in a safe and tolerable way for a user of the final product. In some embodiments, a "cosmetically acceptable" component can facilitate the absorption of one or more active ingredients under application.

Cosmetically acceptable excipients include, without limitation, chelating agents, surfactants, solvents, pH-adjusting agents, skin protection agents, antioxidants, tonics, preservatives, opacifiers, antistatics, moisturizers, antiseborrheic agents, emollients, photoprotectors, emulsifiers and vehicles.

Examples of chelating agents include, without limitation, disodium EDTA, Pentasodium DTPA (Diethylenetriaminepentaacetate Pentasodium), tetrasodium EDTA.

Examples of surfactants include, without limitation, PEG-40 hydrogenated castor oil, Ethoxylated Sorbitan Monoleate (polysorbate 80), Sorbitan Monolaurate (Span 20).

Examples of solvents include, without limitation, methylpropanediol, propylene glycol, pentylene glycol.

Examples of pH adjusting agents include, without limitation, sodium hydroxide, citric acid.

Examples of skin protection agents include, without limitation, *Physalis angulata* extract, Glycerin, acetyl-cyclodextrin, allantoin, Aloe vera callus extract, *Artemisia abrotanum* extract, *Vitis vinifera.*

Examples of antioxidants include, without limitation, tocopherol, BHT, BHA.

Examples of tonics include, without limitation, *Medicago sativa* extract, *Achillea millefolium* extract, *Aesculus chinensis* extract, *Angelica archangelica* leaf extract.

Examples of preservatives include, without limitation, phenoxyethanol, methylisothiazolinone, methylchloroisothiazolinone, methylparaben, propylparaben.

Examples of opacifiers include, without limitation, styrene-acrylate copolymer, alumina, aluminum silicate, glycol stearate.

Examples of vehicles include, without limitation, water, Butylene Glycol, C12-14 isoparaffin.

Examples of moisturizers include, without limitation, *Jasminum officinale* leaf/flower extract, dimethiconol, *Helianthus annuus* petal extract, PCA, *Prunus persica* Fruit Extract.

Examples of emollients include, without limitation, *Fucus vesiculosus* Extract, *Avena sativa* Grain Extract, undecane, *Zea mays* wheat germ oil.

Examples of antiseborrheic agents include, without limitation, *Coriandrum sativum* fruit/leaf extract, biotin, *Camellia sinensis* flower water, phloretin.

Examples of photoprotectors include Benzotriazolyl Dodecyl p-Cresol, benzophenone, benzyl salicylate, homosalate, without limitations.

Examples of Emulsifiers include, without limitation, Sorbitan Olivate, Glycerol Oleate Citrate, Xanthan Gum.

Examples of vehicles include, without limitation, water, esters in general, mineral oil and vegetable oils and mixtures thereof, when in an emulsified system.

The cosmetic composition can be presented in several forms, including, without limitation, solution, suspension, cream, gel, lotion and serum. A person skilled in the art will recognize that the cosmetic form will be defined by the choice of cosmetically acceptable excipients and that the absorption/action of the different active ingredients may vary according to the selected cosmetic form.

The concentration ranges for each component of the dermocosmetic formulation of the present invention are described below.

Conditioning agents are present in the formulation of the present invention in a concentration range from 0.0002 to 35.0000% (w/w).

Chelating agents are present in a concentration from 0.1000 to 2.0000% (w/w).

Surfactants are present in concentrations ranging from 0.1000 to 12.5000% (w/w).

The solvents are present in concentrations ranging from 0.0500 to 25.0000% (w/w).

The pH adjusting agents are present in a concentration range from 0.0150 to 0.5000% (w/w).

Protective agents are present in a concentration range that varies from 0.0100 to 5.0000% (w/w).

Antioxidants are present in a concentration range that varies from 0.0002% to 3.0000 (w/w).

The tonics are present in a concentration range that varies from 0.1900% to 3.5000 (w/w).

Preservatives are present in a concentration range from 0.0150 to 2.5000% (w/w).

Opacifiers are present in a concentration range from 0.0083 to 1.5000% (w/w).

Moisturizing agents are present in a concentration range from 0.0002 to 5.0000% (w/w)

Antiseborrheic agents are present in a concentration range from 0.0002 to 5.0000% (w/w)

Emollient agents are present in a concentration range from 0.0002 to 5.0000% (w/w).

Photoprotective agents are present in a concentration range from 0.1000 to 10.0000% (w/w).

Emulsifying agents are present in a concentration range from 0.1000 to 10.0000% (w/w).

Finally, the concentrations of vehicle vary from 0.0088 to 80.0000% (w/w).

Examples

It should be understood that the examples and embodiments described herein in detail illustrate the present invention without, however, limiting its scope, and that various modifications or changes, in the light of the same, will be suggestive to those skilled in the art. Such equivalent achievements must be included within the scope of the accompanying claims.

The experimental conditions adopted, through the use of human cells in optimal cultivation conditions, are consistent with the current methodologies applied, accepted and validated by the international scientific community. Human cell cultures were purchased commercially from qualified and certified international companies.

Example 1: Effects on Collagen Synthesis in Human Fibroblast Cultures Under Simulated Solar Radiation Conditions Example 1.1: Human Fibroblast Culture Human fibroblasts were seeded in 75 cm$^2$ bottles, grown and expanded in a humid greenhouse at 37° C. in the presence of 5% $CO_2$, using specific culture medium. Upon reaching 70-80% confluence, the cells were seeded in 06-well plates for further incubation with the cosmetic composition of the invention.

Example 1.2: Incubation with the Cosmetic Composition of the Invention and Irradiation Cell cultures were incubated with 3 non-cytotoxic concentrations of the cosmetic composition of the invention (0.78; 0.39; 0.195% (w/v)), determined by the cytotoxicity assay. An ultraviolet radiation simulator (SOL-500; Honle) was used to emit UVA/UVB/VIS (3 J/cm$^2$). After irradiation, the cells remained in contact with the test product under the same conditions described above for an additional 48 hours.

Example 1.3: Collagen Quantification

Soluble collagen (represented in I+IV) was measured using an appropriate commercial kit (SIRCOL™ Soluble Collagen Assay, Biocolor Co., UK). In plastic tubes suitable for microcentrifuge, 1 mL of the specific dye (Sircol™ Dye Reagent) was added to 1000 of the test samples and stirred in an orbital shaker for 30 minutes at room temperature (RT). The formed collagen-dye complex was precipitated by centrifugation (10,000×g) for 10 minutes, the supernatant was then discarded and the button (collagen+dye complex) was resuspended in 1 ml of alkali reagent (0.5 M NaOH solution). 200 μL aliquots were transferred to a 96-well plate and absorbances determined at 540 nm. Collagen concentration was performed based on the calibration curve using standard collagen.

Example 1.4: Statistical Analysis

For statistical analysis, analysis of variance (ANOVA) was used. Dunnett test was used when the analysis of variance detected significant differences between groups. In all groups studied, those whose P values were less than 0.05 were considered statistically significant.

Example 1.5: Results

Figure 1:
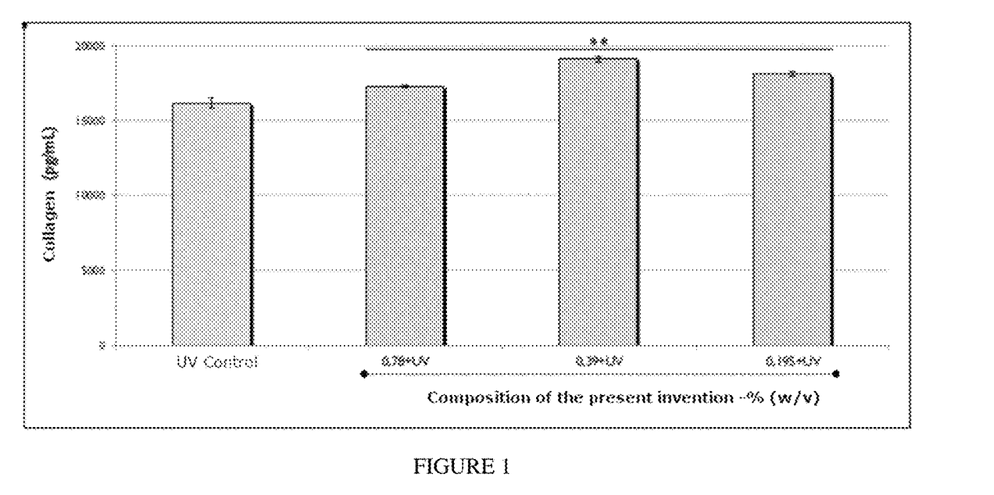
FIG. 1 shows a graph with the results of the effects of the cosmetic composition of the present invention on the synthesis of collagen in human fibroblast culture under conditions of simulated solar radiation.

The results obtained, expressed in Table 1 below, and in FIG. 1, demonstrate the quantification of collagen synthesis. It is possible to observe that the cosmetic composition of the invention, at the evaluated concentrations of 0.78, 0.39 and 0.195% (w/v), was able to significantly increase collagen synthesis by 7, 18 and 12%, respectively when compared with the UV control group.

TABLE 1

| Concentration (% (w/v)) | V1 | V2 | V3 | V4 | Medium | DP |
|---|---|---|---|---|---|---|
| UV control | 16136.00 | 16136.00 | 16136.00 | 16136.00 | 16136.00 | 16136.00 |
| 0.78 | 17126.00 | 17126.00 | 17126.00 | 17126.00 | 17126.00 | 17126.00 |
| 0.39 | 19256.00 | 19256.00 | 19256.00 | 19256.00 | 19256.00 | 19256.00 |
| 0.195 | 18276.00 | 18276.00 | 18276.00 | 18276.00 | 18276.00 | 18276.00 |

Example 2: Effects on Protein Synthesis of Elastin in Human Fibroblast Culture Under Simulated Solar Radiation Conditions

Example 2.1: Human Fibroblast Culture

Human fibroblasts (Gibco, Thermo Scientific, USA) were seeded in 75 cm$^2$ bottles, grown and expanded in a humid oven at 37° C. in the presence of 5% $CO_2$, using specific culture medium. Upon reaching 70-80% confluence, the cells were seeded in 06-well plates for further incubation with the cosmetic composition of the invention.

Example 2.2: Incubation with the Cosmetic Composition of the Invention and Irradiation Cell cultures were incubated with 3 non-cytotoxic concentrations of the cosmetic composition of the invention (0.78; 0.39; 0.195% (w/v)), determined by the cytotoxicity assay. An ultraviolet radiation simulator (SOL-500; Honle) was used to emit UVA/UVB/VIS (3 J/cm$^2$). After irradiation, the cells remained in contact with the cosmetic composition of the invention under the same conditions described above for an additional 48 hours.

Example 2.3: Elastin Quantification

Elastin levels were determined according to the protocol described in the Fastin detection kit (Biocolor, Belfast, Ireland). The elastin content of the samples was precipitated in microcentrifuge tubes after the addition of 1 mL of precipitation reagent (trichloroacetic acid and arginine) and incubation at 0° C. for 24 hours. After centrifuging the tubes (10,000×g) for 10 minutes, the supernatant was discarded and the elastin button resuspended in 1 mL of TPPS (5,10, 15,20-tetraphenyl-21,23-porphine sulfonate) and 200 μL of 90% saturated ammonium sulfate for the formation of the elastin-dye complex. After 60 minutes of stirring, the tubes were again centrifuged (10,000×g) for 10 minutes, the supernatant discarded and the complex resuspended in 1 mL of the dissociation reagent (HCl guanidine and 1-propanol) which allowed the formation of the colored complex, whose absorbance was measured at 513 nm. The elastin concentration was calculated based on the calibration curve using standard elastin provided by the kit manufacturer.

Example 2.4: Statistical Analysis

For statistical analysis, analysis of variance (ANOVA) was used. Dunett test was used when the analysis of variance detected significant differences between groups. In all groups studied, those whose P values were less than 0.05 were considered statistically significant.

Example 2.5: Results

Figure 2:
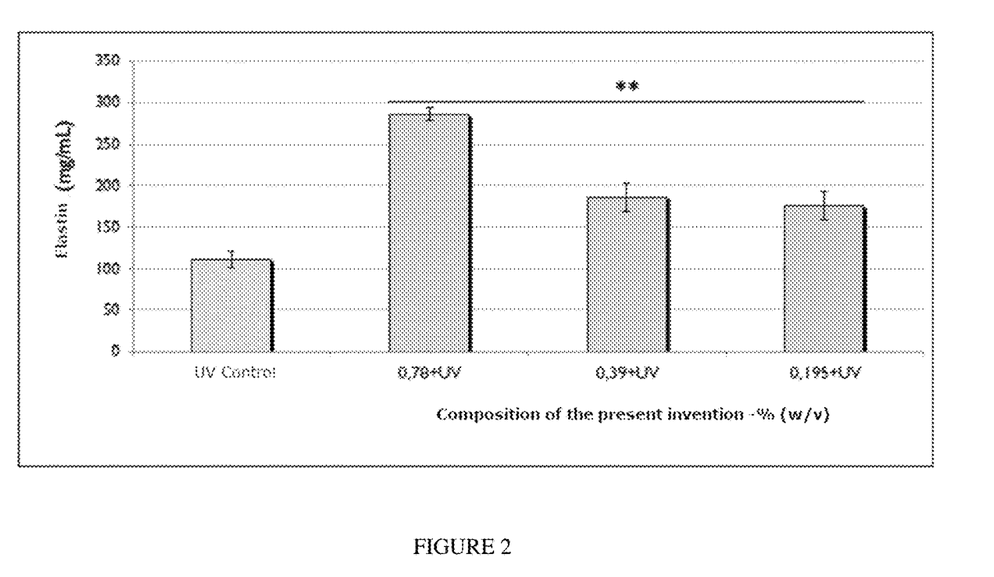
FIG. 2 shows a graph with the results of the effects of the cosmetic composition of the present invention on the synthesis of elastin in human fibroblast culture under conditions of simulated solar radiation.

The results obtained, expressed in Table 2 below, and in FIG. 2, demonstrate the quantification of elastin protein synthesis. It is possible to observe that the cosmetic composition of the invention, in the evaluated concentrations of 0.78, 0.39 and 0.195% (w/v), was able to significantly increase the synthesis of elastin by 157, 68 and 59%, respectively when compared with the UV control group.

TABLE 2

| Concentration (% (w/v)) | V1 | V2 | V3 | V4 | Medium | DP |
|---|---|---|---|---|---|---|
| UV control | 101.40 | 124.80 | 103.90 | 114.80 | 111.21 | 10.72 |
| 0.78 | 294.80 | 276.40 | 283.10 | 288.90 | 285.79 | 7.86 |
| 0.39 | 163.10 | 191.40 | 192.30 | 202.30 | 187.25 | 16.85 |
| 0.195 | 152.30 | 180.60 | 182.30 | 190.60 | 176.42 | 16.69 |

Example 3: Effects on Protein Synthesis of Glycosaminoglycans (Gags) in Human Fibroblast Cultures Under Simulated Solar Radiation Conditions

Example 3.1: Human Fibroblast Culture

Human fibroblasts (Gibco, Thermo Scientific, USA) were seeded in 75 cm$^2$ bottles, grown and expanded in a humid greenhouse at 37° C. in the presence of 5% $CO_2$, using specific culture medium. Upon reaching 70-80% confluence, the cells were seeded in 06-well plates for further incubation with the cosmetic composition of the present invention.

Example 3.2: Incubation with the Cosmetic Composition of the Invention and Irradiation Cell cultures were incubated with 3 non-cytotoxic concentrations of the cosmetic composition of the present invention (0.78, 0.39, 0.195% (w/v)), determined by the cytotoxicity assay. An ultraviolet radiation simulator (SOL-500; Honle) was used to emit UVA/UVB/VIS (3 J/cm$^2$). After irradiation, the cells remained in contact with the test product under the same conditions described above for an additional 48 hours.

Example 3.3: Quantification of GAG

GAG was measured using an appropriate commercial kit (BLYSCAN™ Sulfated Glycosaminoglycan Assay, Biocolor Co., UK). In plastic tubes suitable for microcentrifuge, 1 mL of the specific dye (Blyscan™ Dye Reagent) was added to 100 µl of the test samples and stirred in an orbital shaker for 30 minutes at room temperature (RT). The GAG-dye complex formed was precipitated by centrifugation (12,000 rpm) for 10 minutes, the supernatant was then discarded and the button (GAG sulfate+dye complex) was resuspended in 0.5 ml of dissociation reagent. 200 µL aliquots were transferred to a 96-well plate and the absorbances determined at 656 nm. The concentration of GAG was performed based on the calibration curve using standard GAG.

Example 3.4: Statistical Analysis

For statistical analysis, analysis of variance (ANOVA) was used. Dunnett test was used when the analysis of variance detected significant differences between groups. In all groups studied, those whose P values were less than 0.05 were considered statistically significant.

Example 3.5: Results

Figure 3:
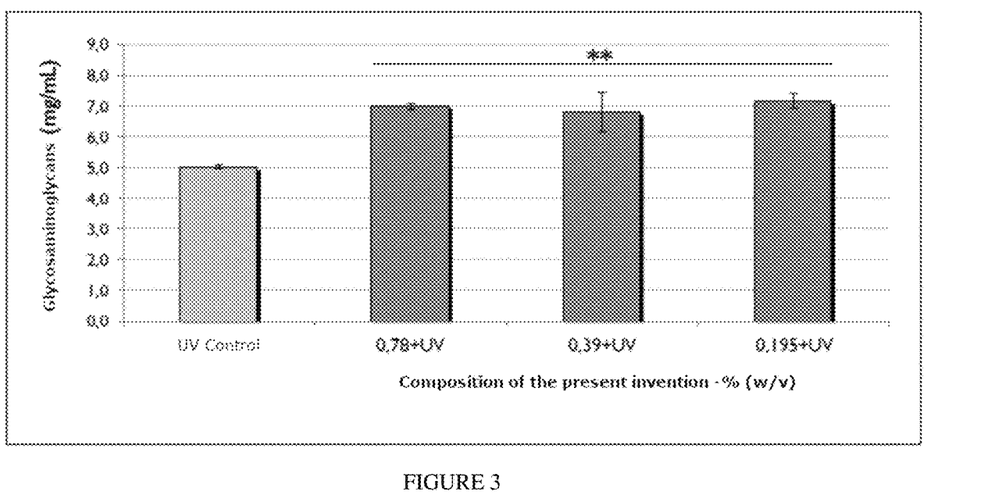
FIG. 3 shows a graph with the results of the effects of the cosmetic composition of the present invention on the synthesis of GAG in human fibroblast culture under conditions of simulated solar radiation.

The results obtained, expressed in Table 3 below, and in FIG. 3, demonstrate the quantification of GAG protein synthesis. It is possible to observe that the cosmetic composition of the invention, under the effects of ultraviolet radiation and in the evaluated concentrations of 0.78, 0.39 and 0.195% (w/v), was able to significantly increase GAG synthesis in 39, 36 and 43%, respectively when compared to the UV control group.

TABLE 3

| Concentration (% (w/v)) | V1 | V2 | V3 | V4 | Medium | DP |
|---|---|---|---|---|---|---|
| UV control | 4.99 | 4.99 | 4.99 | 5.10 | 5.10 | 5.03 |
| 0.78 | 7.10 | 6.89 | 6.89 | 7.00 | 7.10 | 7.00 |
| 0.39 | 7.74 | 6.36 | 6.36 | 7.31 | 7.63 | 7.19 |
| 0.195 | 7.21 | 7.10 | 7.00 | 7.00 | 7.63 | 7.19 |

Example 4: Effects on the Activity of the Superoxide Dismutase Enzyme (SOD) in Human Fibroblast Culture Under Simulated Solar Radiation Stress Conditions

Example 4.1: Human Fibroblast Culture

Human fibroblasts (Gibco, Thermo Scientific, USA) were seeded in 75 cm$^2$ bottles, grown and expanded in a humid greenhouse at 37° C. in the presence of 5% $CO_2$, using specific culture medium. Upon reaching 70-80% confluence, the cells were seeded in 06-well plates for further incubation with the cosmetic composition of the invention.

Example 4.2: Incubation with the Cosmetic Composition of the Invention and Irradiation Cell cultures were incubated with 3 non-cytotoxic concentrations of the cosmetic composition of the invention (0.078, 0.39, 0.195% (w/v)), determined by the cytotoxicity assay. An ultraviolet radiation simulator (SOL-500; Honle) was used to emit UVA/UVB/VIS (3 J/cm$^2$). After irradiation the cells remained in contact with the cosmetic composition of the invention under the same conditions described above for an additional 24 hours.

Example 4.3: Determination of the Activity of the Enzyme Superoxide Dismutase (SOD)

SOD activity was measured in the cell lysate of the cultures using a commercially available assay kit (Cayman Chemical Co., Ann Arbor-MI). The detection of SOD is done with the use of tetrazolium salt to detect superoxide radicals that are generated by the addition of xanthine oxidase to the samples. A unit of SOD is defined as the amount of enzyme needed to promote 50% dismutation of superoxide radicals. SOD activity is calculated based on the known concentration of the SOD standards (U/mL).

Example 4.4: Statistical Analysis

For statistical analysis, analysis of variance (ANOVA) was used. Dunnett test was used when the analysis of variance detected significant differences between groups. In all groups studied, those whose P values were less than 0.05 were considered statistically significant.

Example 4.5: Results

Figure 4:
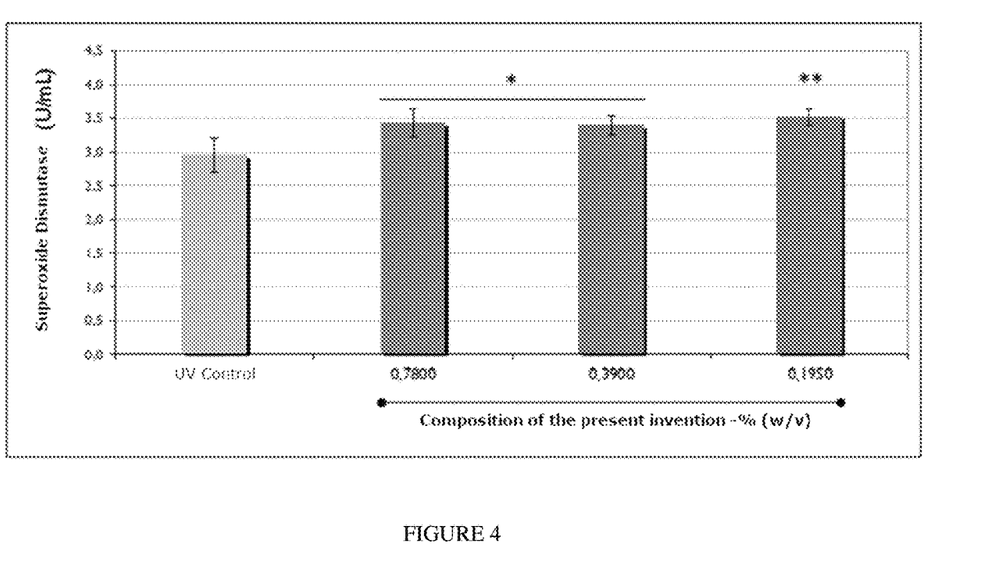
FIG. 4 shows a graph with the results of the effects of the cosmetic composition of the present invention on the activity of the superoxide dismutase enzyme in human fibroblast culture under conditions of simulated solar radiation.

The results obtained, expressed in Table 4 below, and in FIG. 4, demonstrate the increased antioxidant activity promoted. It is possible to observe that the cosmetic composition of the invention, under the effects of ultraviolet radiation and in the evaluated concentrations of 0.78, 0.39 and 0.195% (w/v), was able to significantly increase the activity of the enzyme superoxide dismutase (SOD) in 16, 15 ($P<0.05$) and 20% ($P<0.01$), respectively when compared to the UV control group.

TABLE 4

| Concentration (% (w/v)) | V1 | V2 | V3 | V4 | Medium | DP |
|---|---|---|---|---|---|---|
| UV control | 1.885 | 1.995 | 2.055 | 2.025 | 2.951 | 0.220 |
| 0.78 | 2.097 | 2.130 | 2.164 | 2.211 | 3.426 | 0.143 |
| 0.39 | 2.119 | 2.130 | 2.108 | 2.199 | 3.393 | 0.121 |
| 0.195 | 2.141 | 2.164 | 2.130 | 2.311 | 3.533 | 0.248 |

Example 5: Effects on Cell Proliferation in Human Fibroblast Culture Under Simulated Solar Radiation Stress Conditions Example 5.1: Human Fibroblast Culture Human fibroblasts (Clonetics, Cambrex/Lonza, USA) were seeded in 75 $cm^2$ bottles, grown and expanded in a humid greenhouse at 37° C. in the presence of 5% $CO_2$, using specific culture medium. Upon reaching 70-80% confluence, the cells were trypsinized and seeded in 96-well plates for further incubation with the cosmetic composition of the invention.

Example 5.2: Incubation with the Cosmetic Composition of the Invention and Irradiation Cell cultures were incubated with 3 non-cytotoxic concentrations of each product, previously determined through the cytotoxicity assay. The concentrations evaluated in this study were 0.78, 0.39 and 0.195% (w/v). The cells were kept in contact with the test product for 48 hours for further evaluation of cell proliferation. An ultraviolet radiation simulator (SOL-500; Honle) was used to emit UVA/UVB/VIS (3 $J/cm^2$). After irradiation, the cells remained in contact with the cosmetic composition under the same conditions described above for an additional 24 hours.

Example 5.3: Determination of Cell Proliferation

The cosmetic composition of the invention was diluted in culture medium, in the non-toxic concentrations, defined by the MTT technique. After 48 hours, the BrdU compound was added to the wells in a 1:100 ratio, and the plate was incubated for an additional 4 hours for incorporation into the proliferating cells. Then, the culture medium from each of the wells on the plate was removed, for subsequent addition of a solution capable of denaturing the DNA, followed by a 30 minute incubation at room temperature. Then the solution was removed. Then, the anti-BrdU monoclonal antibody was added to the wells and incubated for 90 minutes at room temperature. Then, the anti-IgG mouse antibody conjugated to the peroxidase was added, and incubation with the antibody for 30 minutes. Afterwards, all wells were washed with specific washing solution. Then, the substrate for peroxidase (TMB) was added, incubated for 5-30 minutes, depending on the intensity of the reaction, at room temperature and protected from light. Then, a solution was added to block the reaction. The reaction was read in a microplate reader at a wavelength of 450 nm. The data obtained were compiled for statistical evaluation.

Example 5.4: Statistical Analysis

For statistical analysis, analysis of variance (ANOVA) was used. Dunnett test was used when the analysis of variance detected significant differences between groups. In all groups studied, those whose P values were less than 0.05 were considered statistically significant.

Example 5.5: Results

Figure 5:
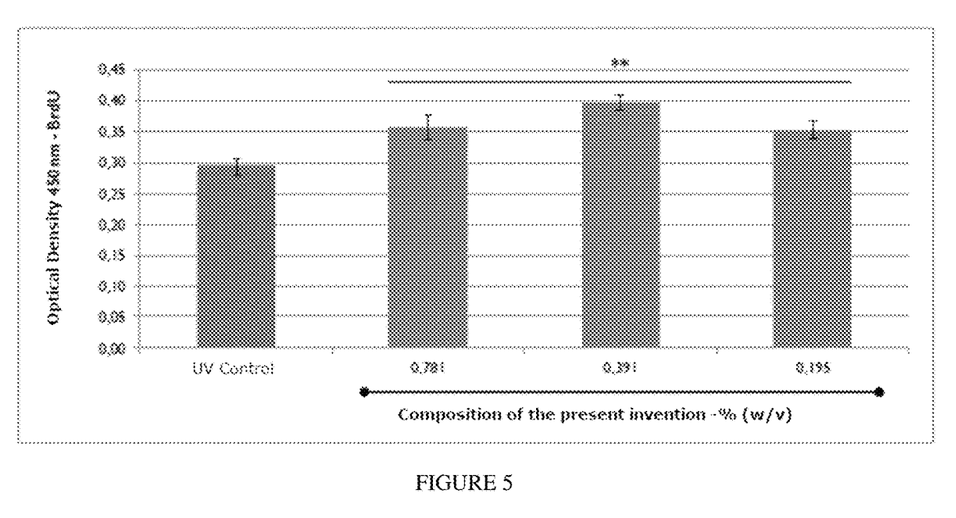
FIG. 5 shows a graph with the results of the effects of the cosmetic composition of the present invention on the rate of cell proliferation of human fibroblasts.

The results obtained, expressed in Table 5 below, and in FIG. 5, demonstrate the increase in cell proliferation. It is possible to observe that the cosmetic composition of the invention, under the effects of ultraviolet radiation and in the evaluated concentrations of 0.781, 0.391 and 0.195% (w/v), was able to increase cell proliferation by 21, 35 and 20%, respectively when compared to the control group under the same conditions.

TABLE 5

| Concentration (% (w/v)) | V1 | V2 | V3 | V4 | Medium | DP |
|---|---|---|---|---|---|---|
| UV control | 0.278 | 0.306 | 0.293 | 0.298 | 0.290 | 0.014 |
| 0.781 | 0.372 | 0.363 | 0.333 | 0.356 | 0.360 | 0.020 |
| 0.391 | 0.386 | 0.385 | 0.407 | 0.395 | 0.400 | 0.012 |
| 0.195 | 0.334 | 0.362 | 0.342 | 0.372 | 0.350 | 0.014 |

Example 6: Examples of Cosmetic Composition

The compounds used in the dermocosmetic formulation of the cosmetic composition of the present invention, their respective weight/weight percentages and their respective functions are found in the examples below.

Example 6.1

| | | |
|---|---|---|
| Aqua | 90.2512 | Vehicle |
| Polysorbate 80 | 1.0000 | Surfactant |
| Cetearyl Olivato | 0.5000 | Conditioning |
| Sorbitan olivate | 0.5000 | Emulsifier |
| Glycerin | 1.4000 | Humectant |
| Olea europaea Leaf Extract | 1.3000 | Conditioning Agent |
| Methylpropanediol | 1.0000 | Solvent |
| Butylene Glycol | 0.9800 | Humectant |
| Sodium hydroxide | 0.5000 | qs pH adjustment |
| Phenoxyethanol | 0.4755 | Preservative |
| Styrene/Acrylate Copolymer | 0.4000 | Opacifier |
| Glycine Soybean Seed Extract | 0.2357 | Conditioning Agent |
| Medicago sativa extract | 0.1900 | Tonic |
| Sodium PCA | 0.1500 | Conditioning Agent |
| Physalis angulata extract | 0.1200 | Skin Protector |
| Sodium Lactate | 0.1200 | Humectant |
| Ramnose | 0.1175 | Humectant |
| Citric acid | 0.1150 | qs pH adjustment |
| Benzotriazolyl Dodecyl p-Cresol | 0.100 | Photoprotector |

-continued

| | | |
|---|---|---|
| Disodium EDTA | 0.100 | Chelating agent |
| Arginine | 0.0800 | Conditioning Agent |
| Propylene glycol | 0.0575 | Humectant |
| Aspartic acid | 0.0520 | Conditioning Agent |
| PCA | 0.0427 | Moisturizer |
| *Prunus mum* fruit extract | 0.0400 | Humectant |
| Biosaccharide gum-2 | 0.02500 | Conditioning Agent |
| *Microcitrus australasica* fruit extract | 0.0200 | Conditioning Agent |
| Silanetriol | 0.0152 | Conditioning Agent |
| *Lavandula angustifolia* extract | 0.0150 | Conditioning Agent |
| Glycine | 0.0128 | Conditioning Agent |
| Alanine | 0.0120 | Conditioning Agent |
| Biosaccharide gum-1 | 0.0110 | Conditioning Agent |
| *Camellia sinensis* Leaf Extract | 0.0090 | Conditioning Agent |
| *Prunus persica* Fruit Extract | 0.0090 | Moisturizer |
| Methylisothiazolinone | 0.00830 | Preservative |
| Serine | 0.0080 | Conditioning Agent |
| Valine | 0.0064 | Conditioning Agent |
| Ethylhexylglycerin | 0.0040 | Conditioning Agent |
| Isoleucine | 0.0040 | Antistatic |
| Proline | 0.0040 | Conditioning Agent |
| Threonine | 0.0040 | Conditioning Agent |
| Histidine | 0.0016 | Conditioning Agent |
| Phenylalanine | 0.0016 | Conditioning Agent |
| Fruit Extract of *Citrus aurantium bergamia* | 0.0002 | Conditioning Agent |
| *Coriandrum sativum* Fruit/Leaf Extract | 0.0002 | Antiseborrheic Agent |
| *Cupressus sempervirens* leaf/stem extract | 0.0002 | Conditioning Agent |
| *Fucus vesiculosus* extract | 0.0002 | Emollient |
| *Jasminum officinale* Leaf/Flower Extract | 0.0002 | Moisturizer |
| *Plumeria rubra* extract | 0.0002 | Conditioning Agent |
| *Rose* Extract | 0.0002 | Conditioning Agent |
| *Rosmarinus officinalis* Leaf Extract | 0.0002 | Conditioning Agent |
| Tocopherol | 0.0002 | Anti-oxidant |
| *Vanilla planifolia* Fruit Extract | 0.0002 | Conditioning Agent |

Example 6.2

| | | |
|---|---|---|
| Aqua | 89.5512 | Vehicle |
| Polysorbate 80 | 1 | Surfactant |
| Glyceryl Citrate Oleate | 0.5 | Emulsifier |
| Capric/Caprylic Triglyceride | 1 | Conditioning Agent |
| Sodium Polyacrylate | 0.119 | Emulsifier |
| Isotridecyl isononanoate | 0.075 | Emollient |
| Trideceth-6 | 0.006 | Emollient |
| Glycerin | 1.4 | Humectant |
| *Olea europaea* leaf extract | 1.3 | Conditioning Agent |

-continued

| | | |
|---|---|---|
| Methylpropanediol | 1 | Solvent |
| Butylene Glycol | 0.98 | Humectant |
| Sodium Hydroxide | 0.5 | qs pH adjustment |
| Phenoxyethanol | 0.4755 | Preservative |
| Styrene-acrylate copolymer | 0.4 | Opacifier |
| Glycine Soybean Seed Extract | 0.2357 | Conditioning Agent |
| *Medicago sativa* extract | 0.19 | Tonic |
| Sodium PCA | 0.15 | Conditioning Agent |
| *Physalis angulata* extract | 0.12 | Skin Protector |
| Sodium Lactate | 0.12 | Humectant |
| Ramnose | 0.1175 | Humectant |
| Citric acid | 0.115 | qs pH adjustment |
| Benzotriazolyl Dodecyl p-Cresol | 0.1 | Photoprotector |
| Disodium EDTA | 0.1 | Chelating agent |
| Arginine | 0.08 | Conditioning Agent |
| Propylene glycol | 0.0575 | Humectant |
| Aspartic acid | 0.052 | Conditioning Agent |
| PCA | 0.0427 | Moisturizer |
| *Prunus Mume* Fruit Extract | 0.04 | Humectant |
| Biosaccharide gum-2 | 0.025 | Conditioning Agent |
| *Microcitrus ustralasica* fruit extract | 0.02 | Conditioning Agent |
| Silanetriol | 0.0152 | Conditioning Agent |
| *Lavandula angustifolia* extract | 0.015 | Conditioning Agent |
| Glycine | 0.0128 | Conditioning Agent |
| Alanine | 0.012 | Conditioning Agent |
| Biosaccharide gum-1 | 0.011 | Conditioning Agent |
| *Camellia sinensis* Leaf Extract | 0.009 | Conditioning Agent |
| *Prunus persica* fruit extract | 0.009 | Moisturizer |
| Methylisothiazolinone | 0.0083 | Preservative |
| Serine | 0.008 | Conditioning Agent |
| Valine | 0.0064 | Conditioning Agent |
| Ethylhexylglycerin | 0.004 | Conditioning Agent |
| Isoleucine | 0.004 | Antistatic |
| Proline | 0.004 | Conditioning Agent |
| Threonine | 0.004 | Conditioning Agent |
| Histidine | 0.0016 | Conditioning Agent |
| Phenylalanine | 0.0016 | Conditioning Agent |
| Fruit Extract of *Citrus aurantium bergamia* | 0.0002 | Conditioning Agent |
| *Coriandrum sativum* Fruit/Leaf Extract | 0.0002 | Antiseborrheic Agent |
| *Cupressus sempervirens* leaf/stem extract | 0.0002 | Conditioning Agent |
| *Fucus vesiculosus* extract | 0.0002 | Emollient |
| *Jasminum officinale* Flower/Leaf Extract | 0.0002 | Moisturizer |
| *Plumeria rubra* extract | 0.0002 | Conditioning Agent |
| *Rose* Extract | 0.0002 | Conditioning Agent |
| *Rosmarinus officinalis* Leaf Extract | 0.0002 | Conditioning Agent |
| Tocopherol | 0.0002 | Anti-oxidant |
| *Vanilla planifolia* fruit extract | 0.0002 | Conditioning Agent |

Example 6.3

| | | |
|---|---|---|
| Aqua | 89.5512 | Vehicle |
| Polysorbate 80 | 1 | Surfactant |
| Glyceryl Citrate Oleate | 0.5 | Emulsifier |
| Capric/Caprylic Triglyceride | 1 | Conditioning Agent |
| Xanthan gum | 0.2 | Emulsifier |
| Glycerin | 1.4 | Humectant |
| *Olea europaea* extract | 1.3 | Conditioning Agent |
| Methylpropanediol | 1 | Solvent |
| Butylene Glycol | 0.98 | Humectant |
| Sodium Hydroxide | 0.5 | qs pH adjustment |
| Phenoxyethanol | 0.4755 | Preservative |

-continued

| Ingredient | Amount | Function |
|---|---|---|
| Styrene-Acrylate Copolymer | 0.4 | Opacifier |
| Glycine Soybean Seed Extract | 0.2357 | Conditioning Agent |
| *Medicago sativa* extract | 0.19 | Tonic |
| Sodium PCA | 0.15 | Conditioning Agent |
| *Physalis angulata* extract | 0.12 | Skin Protector |
| Sodium Lactate | 0.12 | Humectant |
| Ramnose | 0.1175 | Humectant |
| Citric acid | 0.115 | qs pH adjustment |
| Benzotriazolyl Dodecyl p-Cresol | 0.1 | Photoprotector |
| Disodium EDTA | 0.1 | Chelating agent |
| Arginine | 0.08 | Conditioning Agent |
| Propylene glycol | 0.0575 | Humectant |
| Aspartic acid | 0.052 | Conditioning Agent |
| PCA | 0.0427 | Moisturizer |
| *Prunus mume* extract | 0.04 | Humectant |
| Biosaccharide gum-2 | 0.025 | Conditioning Agent |
| *Microcitrus australasica* extract | 0.02 | Conditioning Agent |
| Silanetriol | 0.0152 | Conditioning Agent |
| *Lavandula angustifolia* extract | 0.015 | Conditioning Agent |
| Glycine | 0.0128 | Conditioning Agent |
| Alanine | 0.012 | Conditioning Agent |
| Biosaccharide gum-1 | 0.011 | Conditioning Agent |
| *Camellia sinensis* Leaf Extract | 0.009 | Conditioning Agent |
| *Prunus persica* Fruit Extract | 0.009 | Moisturizer |
| Methylisothiazolinone | 0.0083 | Preservative |
| Serine | 0.008 | Conditioning Agent |
| Valine | 0.0064 | Conditioning Agent |
| Ethylhexylglycerin | 0.004 | Conditioning Agent |
| Isoleucine | 0.004 | Antistatic |
| Proline | 0.004 | Conditioning Agent |
| Threonine | 0.004 | Conditioning Agent |
| Histidine | 0.0016 | Conditioning Agent |
| Phenylalanine | 0.0016 | Conditioning Agent |
| *Citrus aurantium bergamia* Fruit Extract | 0.0002 | Conditioning Agent |
| *Coriandrum sativum* Fruit/Leaf Extract | 0.0002 | Antiseborrheic Agent |
| *Cupressus sempervirens* leaf/stem extract | 0.0002 | Conditioning Agent |
| *Fucus vesiculosus* extract | 0.0002 | Emollient |
| *Jasminum officinale* Flower/Leaf Extract | 0.0002 | Moisturizer |
| *Plumeria rubra* Flower Extract | 0.0002 | Conditioning Agent |
| *Rose* Extract | 0.0002 | Conditioning Agent |
| *Rosmarinus officinalis* Leaf Extract | 0.0002 | Conditioning Agent |
| Tocopherol | 0.0002 | Anti-oxidant |
| *Vanilla Planifolia* Fruit Extract | 0.0002 | Conditioning Agent |

Example 6.4

| Ingredient | Amount | Function |
|---|---|---|
| Aqua | 8.7488 | Vehicle |
| Polysorbate 80 | 1.0000 | Surfactant |
| Glycerin | 1.4000 | Humectant |
| *Olea Europaea* Leaf Extract | 1.3000 | Conditioning Agent |
| Methylpropanediol | 1.0000 | Solvent |
| Butylene Glycol | 0.9800 | Humectant |
| Sodium Hydroxide | 0.5000 | qs pH adjustment |
| Phenoxyethanol | 0.4755 | Preservative |
| Styrene-Acrylate Copolymer | 0.4000 | Opacifier |
| Glycine Soybean Seed Extract | 0.2357 | Conditioning Agent |
| *Medicago sativa* extract | 0.1900 | Tonic |
| Sodium PCA | 0.1500 | Conditioning Agent |
| *Physalis angulata* extract | 0.1200 | Skin Protector |
| Sodium Lactate | 0.1200 | Humectant |
| Ramnose | 0.1175 | Humectant |
| Citric acid | 0.115 | qs pH adjustment |
| Benzotriazolyl Dodecyl p-Cresol | 0.1000 | Photoprotector |
| Disodium EDTA | 0.1000 | Chelating agent |
| Arginine | 0.0800 | Conditioning Agent |
| Propylene glycol | 0.0575 | Humectant |
| Aspartic acid | 0.0520 | Conditioning Agent |
| PCA | 0.0427 | Moisturizer |
| *Prunus mume* Fruit Extract | 0.0400 | Humectant |
| Biosaccharide gum-2 | 0.0250 | Conditioning Agent |
| *Microcitrus australasica* Fruit Extract | 0.0200 | Conditioning Agent |
| Silanetriol | 0.0152 | Conditioning Agent |
| *Lavandula angustifolia* extract | 0.0150 | Conditioning Agent |
| Glycine | 0.0128 | Conditioning Agent |
| Alanine | 0.0120 | Conditioning Agent |
| Biosaccharide gum-1 | 0.0110 | Conditioning Agent |
| *Camellia sinensis* Leaf Extract | 0.0090 | Conditioning Agent |
| *Prunus persica* Fruit Extract | 0.0090 | Moisturizer |
| Methylisothiazolinone | 0.0083 | Preservative |
| Serine | 0.0080 | Conditioning Agent |
| Valine | 0.0064 | Conditioning Agent |
| Ethylhexylglycerin | 0.0040 | Conditioning Agent |
| Isoleucine | 0.0040 | Antistatic |
| Proline | 0.0040 | Conditioning Agent |
| Threonine | 0.0040 | Conditioning Agent |
| Histidine | 0.0016 | Conditioning Agent |
| Phenylalanine | 0.0016 | Conditioning Agent |
| Fruit Extract of *Citrus aurantium bergamia* | 0.0002 | Conditioning Agent |
| *Coriandrum sativum* Fruit/Leaf Extract | 0.0002 | Antiseborrheic Agent |
| *Cupressus sempervirens* leaf/stem extract | 0.0002 | Conditioning Agent |
| *Fucus vesiculosus* extract | 0.0002 | Emollient |
| *Jasminum officinale* Flower/Leaf Extract | 0.0002 | Moisturizer |
| *Plumeria rubra* Flower Extract | 0.0002 | Conditioning Agent |
| *Rose* Extract | 0.0002 | Conditioning Agent |
| *Rosmarinus officinalis* Leaf Extract | 0.0002 | Conditioning Agent |
| Tocopherol | 0.0002 | Anti-oxidant |
| *Vanilla Planifolia* Fruit Extract | 0.0002 | Conditioning Agent |

Example 7

In a preferred embodiment, the compounds used in the formulation of the cosmetic composition of the present invention, their respective weight/weight percentages and their respective functions are found in Table 7.

TABLE 7

| Ingredient | Amount | Function |
|---|---|---|
| Aqua | 78.8413 | Vehicle |
| PEG-40 Hydrogenated Castor Oil | 8.0000 | Surfactant |
| Capric/Caprylic Triglyceride | 5.4099 | Conditioning Agent |
| Glycerin | 1.4000 | Humectant |
| *Olea europaea* Leaf Extract | 1.3000 | Conditioning Agent |
| Methylpropanediol | 1.0000 | Solvent |
| Butylene Glycol | 0.9800 | Humectant |
| Sodium Hydroxide | 0.5000 | qs pH adjustment |
| Phenoxyethanol | 0.4755 | Preservative |
| Styrene-Acrylate Copolymer | 0.4000 | Opacifier |
| Glycine Soybean Seed Extract | 0.2357 | Conditioning Agent |
| *Medicago sativa* extract | 0.1900 | Tonic |
| Sodium PCA | 0.1500 | Conditioning Agent |
| *Physalis angulata* extract | 0.1200 | Skin Protector |
| Sodium Lactate | 0.1200 | Humectant |
| Ramnose | 0.1175 | Humectant |

TABLE 7-continued

| | | |
|---|---|---|
| Citric acid | 0.115 | qs pH adjustment |
| Benzotriazolyl Dodecyl p-Cresol | 0.1000 | Photoprotector |
| Disodium EDTA | 0.1000 | Chelating agent |
| Arginine | 0.0800 | Conditioning Agent |
| Propylene glycol | 0.0575 | Humectant |
| Aspartic acid | 0.0520 | Conditioning Agent |
| PCA | 0.0427 | Moisturizer |
| *Prunus mume* Fruit Extract | 0.0400 | Humectant |
| Biosaccharide gum-2 | 0.0250 | Conditioning Agent |
| *Microcitrus australasica* Fruit Extract | 0.0200 | Conditioning Agent |
| Silanetriol | 0.0152 | Conditioning Agent |
| *Lavandula angustifolia* extract | 0.0150 | Conditioning Agent |
| Glycine | 0.0128 | Conditioning Agent |
| Alanine | 0.0120 | Conditioning Agent |
| Biosaccharide gum-1 | 0.0110 | Conditioning Agent |
| *Camellia sinensis* Leaf Extract | 0.0090 | Conditioning Agent |
| *Prunus persica* Fruit Extract | 0.0090 | Moisturizer |
| Methylisothiazolinone | 0.0083 | Preservative |
| Serine | 0.0080 | Conditioning Agent |
| Valine | 0.0064 | Conditioning Agent |
| Ethylhexylglycerin | 0.0040 | Conditioning Agent |
| Isoleucine | 0.0040 | Antistatic |
| Proline | 0.0040 | Conditioning Agent |
| Threonine | 0.0040 | Conditioning Agent |
| Histidine | 0.0016 | Conditioning Agent |
| Phenylalanine | 0.0016 | Conditioning Agent |
| Fruit Extract of *Citrus aurantium bergamia* | 0.0002 | Conditioning Agent |
| *Coriandrum sativum* Fruit/Leaf Extract | 0.0002 | Antiseborrheic Agent |
| *Cupressus sempervirens* leaf/stem extract | 0.0002 | Conditioning Agent |
| *Fucus vesiculosus* extract | 0.0002 | Emollient |
| *Jasminum officinale* Flower/Leaf Extract | 0.0002 | Moisturizer |
| *Plumeria rubra* Flower Extract | 0.0002 | Conditioning Agent |
| *Rose* Extract | 0.0002 | Conditioning Agent |
| *Rosmarinus officinalis* Leaf Extract | 0.0002 | Conditioning Agent |
| Tocopherol | 0.0002 | Anti-oxidant |
| *Vanilla Planifolia* Fruit Extract | 0.0002 | Conditioning Agent |

CONCLUSIONS

In relation to Example 1, it is possible to conclude that the cosmetic composition of the present invention was able to increase up to 18% the collagen synthesis, when compared with the UV Control group, under the same conditions. And yet, it demonstrated the protective capacity of the skin being able to protect and stimulate the collagen synthesis.

In relation to Example 2, it is possible to conclude that the cosmetic composition of the present invention, in culture of human fibroblasts and under ultraviolet radiation, is able to act in the fight against photoaging by increasing up to 157% of the protein synthesis of elastin, when compared with the control group, under the same conditions. It was also possible to observe the ability of said composition to protect and stimulate the synthesis of elastin.

Considering the results presented in Example 3, the cosmetic composition of the invention, in human fibroblast culture, was able to increase up to 43% the GAG synthesis, when compared to the Control group, in addition to having demonstrated the ability to protect and stimulate the GAG synthesis.

The results of Example 4 allow us to conclude that the cosmetic composition of the present invention, in human fibroblast culture, increased by up to 20% the activity of the superoxide dismutase enzyme (SOD) when compared to the control group under the same conditions.

Finally, Example 5 presents results that demonstrate that the cosmetic composition of the present invention, in fibroblast culture and under the effect of solar radiation, was able to increase the cell proliferation by up to 35%, when compared to the control group.

Although certain embodiments have been described in a specific way, they have been presented only as an example, and there is no intention to limit the scope of the invention. The claims that accompany this description and their equivalents are considered to cover such embodiments.

Finally, modifications of the present invention, evident to a person skilled in the art, such as adding or removing elements that are not fundamental to its implementation, can be carried out without departing from the scope and spirit of the invention.

REFERENCES

1. Wan H, Williams R, Doherty P, Williams Df. A study of the reproducibility of the MTT test. Journal of materials science 1994; 5: 154-159.
2. Bank u, reinhold d, ansorge s. Measurement of cellular activity with the MTT test. Optimization of the method. Allerg immunol; 1991 37(3-4): 119-23.

The invention claimed is:

1. A cosmetic composition comprising a combination of sodium PCA, sodium lactate, arginine, aspartic acid, PCA, glycine, alanine, serine, valine, proline, threonine, isoleucine, histidine, phenylalanine, *Olea europaea* leaf extract, butylene glycol, *Prunus* mume fruit extract, silanetriol, rhamnose, *Medicago sativa* extract, ethylhexylglycerin, glycerin, *Microcitrus australasica* fruit extract, biosaccharide gum-1, biosaccharide gum-2, *Physalis angulata* extract, caprylic, and capric triglyceride.

2. The cosmetic composition of claim 1, wherein the composition further comprises moisturizing agents, chelating agents and/or cosmetically acceptable excipients.

3. The cosmetic composition of claim 2, wherein the cosmetically acceptable excipients include surfactants, solvents, pH adjusting agents, skin protection agents, antioxidants, tonics, preservatives, opacifiers, antistats, emollients, antiseborrheic agents, photoprotectors, emulsifiers and/or vehicles.

4. The cosmetic composition of claim 3, wherein the pH adjusting agents have a concentration ranging from 0.0150 to 0.5000% (w/w).

5. The cosmetic composition of claim 2, wherein the moisturizing agents have a concentration ranging from 0.0002 to 5.0000% (w/w).

6. The cosmetic composition of claim 3, wherein the preservatives have a concentration ranging 0.0150 to 2.5000% (w/w).

7. The cosmetic composition of claim 3, wherein the emollients have a concentration ranging from 0.0002 to 5.0000% (w/w).

8. The cosmetic composition of claim 2, wherein the chelating agents have a concentration ranging from 0.1000 to 2.0000% (w/w).

9. The cosmetic composition of claim 3, wherein the skin protection agents have a concentration ranging from 0.0100 to 5.0000% (w/w).

10. The cosmetic composition of claim 3, wherein the antiseborrheic agents have a concentration ranging from 0.0002 to 5.0000% (w/w).

11. The cosmetic composition of claim 3, wherein the surfactants have a concentration ranging from 0.1000 to 12.5000% (w/w).

12. The cosmetic composition of claim 3, wherein the tonics have a concentration ranging from 0.1900% to 3.5000% (w/w).

13. The cosmetic composition of claim 3, wherein the vehicles have a concentration ranging from 0.0088 to 80.0000% (w/w).

14. The cosmetic composition of claim 3, wherein the pH adjusting agents are sodium hydroxide or citric acid.

15. The cosmetic composition of claim 2, wherein the chelating agents are selected from the group consisting of disodium EDTA, pentasodium DTPA (diethylenetriamine-pentaacetate pentasodium) and tetrasodium EDTA.

16. The cosmetic composition of claim 3, wherein the preservatives are selected from the group consisting of phenoxyethanol, methylisothiazolinone, methylchloroiso-thiazolinone, methylparaben and propylparaben.

17. The cosmetic composition of claim 3, wherein the emollients are selected from the group consisting of *Fucus Vesiculosus* extract, *Avena sativa* grain extract, undecane and *Zea mays* wheat germ oil.

18. The cosmetic composition of claim 3, wherein the antiseborrheic agents are selected from the group consisting of *Coriandrum sativum* fruit/leaf extract, biotin, *Camellia sinensis* flower water and Phloretin.

19. The cosmetic composition of claim 3, wherein the surfactants are selected from the group consisting of hydrogenated castor oil PEG-40, ethoxylated sorbitan monoleate and sorbitan monolaurate.

20. The cosmetic composition of claim 3, wherein the tonics are selected from the group consisting of *Achillea millefolium* extract, *Aesculus chinensis* extract and *Angelica archangelica* leaf extract.

21. The cosmetic composition of claim 3, wherein the vehicles are selected from the group consisting of water, esters in general, mineral oil and vegetable oils and mixtures thereof, when in an emulsified system.

22. A dermocosmetic formulation comprising the composition of claim 1 presented as a solution, suspension, cream, gel, lotion or serum.

23. The cosmetic composition as defined of claim wherein the composition acts on the synthesis of collagen, elastin and glycosaminoglycans (GAG), on the activity of the superoxide dismutase enzyme (SOD) and on the increase of cell proliferation.

24. The cosmetic composition of claim 23, wherein the composition combats skin aging or photoaging.

* * * * *